US006965059B1

(12) United States Patent
Granados et al.

(10) Patent No.: US 6,965,059 B1
(45) Date of Patent: Nov. 15, 2005

(54) METHOD OF PROTECTING PLANTS BY INTRODUCING A GENE CODED FOR A PROTEIN WHICH ENHANCES VIRUS INFECTION OF HOST INSECTS

(75) Inventors: Robert R. Granados, Ithaca, NY (US); Yoshifumi Hashimoto, Kyoto (JP)

(73) Assignee: Boyce Thompson Institute for Plant Research, Inc., Ithaca, NY (US)

( * ) Notice: Subject to any disclaimer, the term of this patent is extended or adjusted under 35 U.S.C. 154(b) by 0 days.

(21) Appl. No.: 08/091,655

(22) Filed: Jul. 14, 1993

Related U.S. Application Data

(63) Continuation-in-part of application No. 07/971,624, filed on Nov. 4, 1992, now Pat. No. 5,475,090, which is a continuation-in-part of application No. 07/663,560, filed on Mar. 4, 1991, now abandoned, which is a continuation-in-part of application No. 07/313,226, filed on Feb. 21, 1989, now abandoned.

(51) Int. Cl.$^7$ ............................. C12N 15/82; A01H 5/00
(52) U.S. Cl. ......................... 800/279; 435/419; 435/468
(58) Field of Search ................................. 800/279, 302, 800/205; 435/419, 468, 172.1; 935/34, 64; 536/23.2

(56) References Cited

U.S. PATENT DOCUMENTS

| | | | | |
|---|---|---|---|---|
| 4,394,443 A | * | 7/1983 | Weissman et al. | 435/6 |
| 4,446,235 A | * | 5/1984 | Seeburg | 435/91 |
| 4,675,285 A | * | 6/1987 | Clark et al. | 435/6 |
| 4,973,667 A | * | 11/1990 | Granados | 530/350 |
| 5,011,685 A | | 4/1991 | Granados | 424/93 |
| 5,475,090 A | | 12/1995 | Granados et al. | 530/350 |

FOREIGN PATENT DOCUMENTS

| | | | | |
|---|---|---|---|---|
| EP | 0142924 | * | 5/1985 | |
| WO | WO97/08197 | | 3/1997 | C07K/14/01 |

OTHER PUBLICATIONS

Hashimoto et al 1991 J of Gen Vir. 72 : 2645–2651.*
Wilke–Douglas et al 1986 Physical Plantacum 68 : 560–565.*
Brunks et al 1991 Trends in Biotechnology 9 : 197–200.*
Beard 1989 New Scientist No. 1696/1697 p. 21.*
Yamamoto et al 1979 J. Gen. Virology 45 : 371–381.*
Hashimoto, Yoshifumi et al. "Location and Nucleotide Sequence of the Gene Encoding the Viral Enhancing Factor of the *Trichoplusia ni* Granulosis Virus" Journal of General Virology 1991 p. 2646–2651.
Shuler, M.L. et al. (EDS) "Baculovirus Express Systems and Biopesticides" 1995, John Wiley and Sons, New York, US.
Roelvink, Peter W. et al. "Characterization of the Helicoverpa Armigera and Pseudaletia Unipuncta Granulovirus Enhancin Genes" Journal of General Virology 1995 p. 2693–2705.
Horsch, R. et al, "A Simple and General Method for Transferring Genes into Plants", Science vol 227, Mar. 1985, pp 1229–1231.
Hoekema, A. et al, "A binary plant vector strategy based on separation of vir and T–region of the Agrobacterium tubefaciens Ta–plasmid" Nature vol. 303, May 1983, pp 179–180.
Datta, G. et al., "Broad hosst range DNA cloning system for Gram–negative bacteria; Constuction of a gene bank of *Rhizobium meliloti*" Proc. Natl. Acad. Sci. USA, vol. 77, Dec. 1980, pp 7374–7351.
Bevan, M., "Binary Agrobacterium vectors for plant transformation", Nucleic Acids Res., vol. 12, 1984, pp. 8711–8721.

* cited by examiner

*Primary Examiner*—Elizabeth F. McElwain
(74) *Attorney, Agent, or Firm*—Brown & Michaels, PC

(57) ABSTRACT

Recent advances of the research on synergistic effect of a mixed baculovirus infection demonstrated the presence of viral molecules enhancing the early event of infection. The enhancins from the *Trichoplusia ni* was identified to have such a function, i.e., disrupting the structural integrity of peritrophic membrane of midgut of *T. ni* larva. The enhancin gene was ligated downstream of the CaMV 355 promoter of a binary vector pBI121. With a drug resistant gene, the gene was introduced to a piece of tobacco leaf, from *Nicotiana tobacum* cv. Havana SR1. We screened 11 regenerated plants out of 37 by feeding tobacco powder mixed in artificial diet, to 3rd instar *Pseudaletia separata* larvae. The larval stage was usually delayed from 1 to 3 days in comparison of that of control larvae. The larvae did not pupate normally. The larvae showed irregular morphology of half larva and half pupae, suggesting a hormonal disturbance caused by the transgenic tobacco. The introduction of an enhancin gene into plants is an effective method of protecting them from insects due to the disruption of their normal life cycle.

8 Claims, 5 Drawing Sheets

Figure 1:
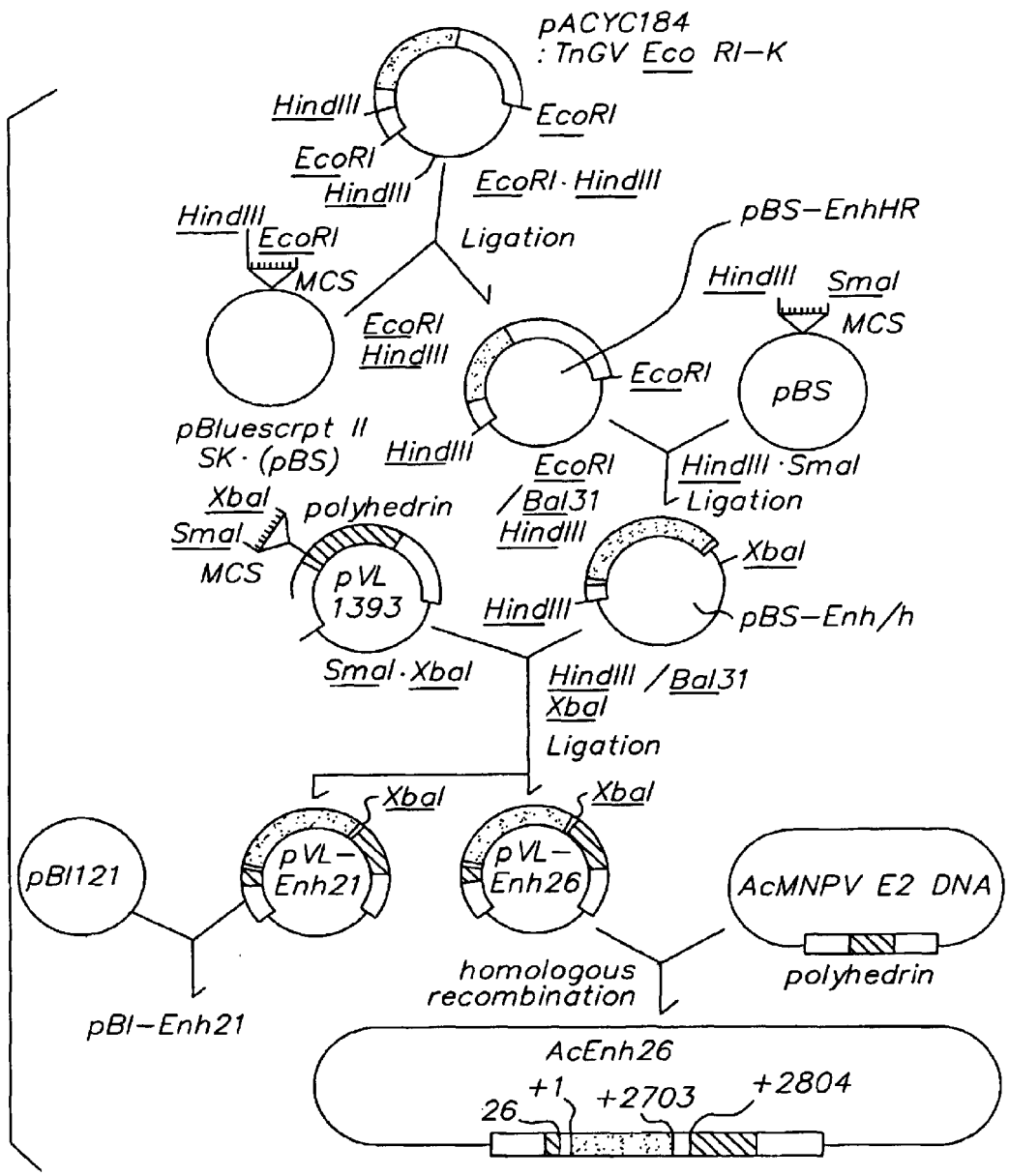
Figure 2:
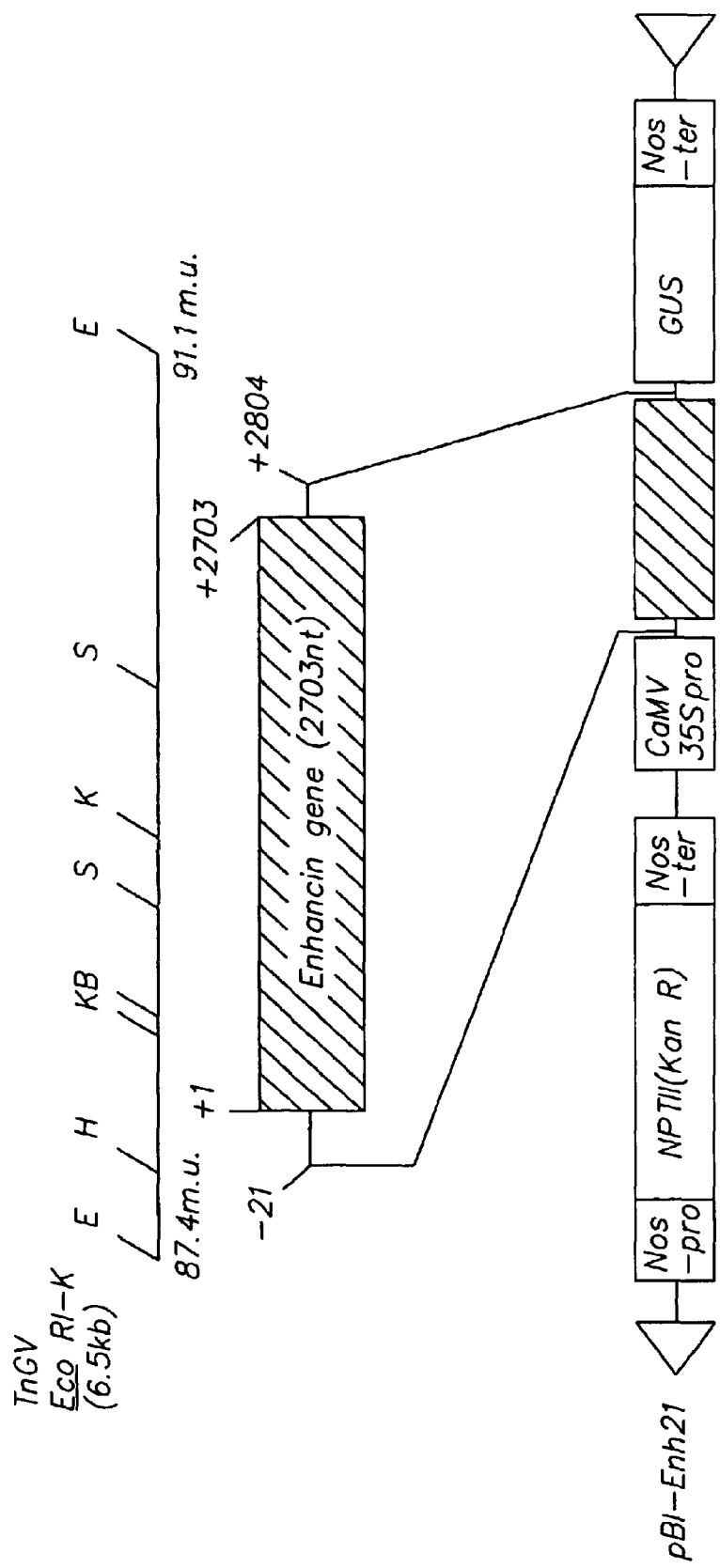
Figure 3:
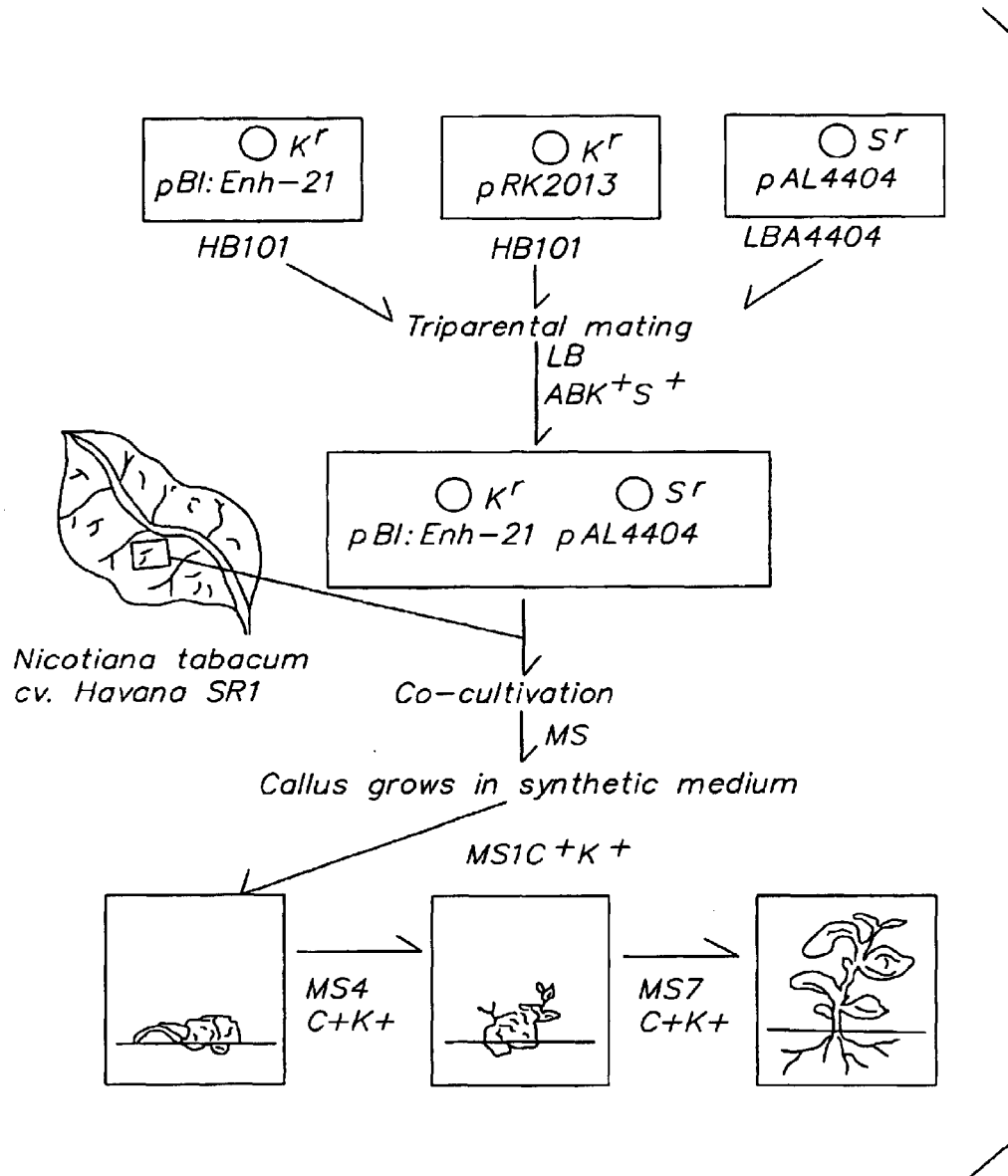

Pupae of Pseudaletia separata fed with transgenic tobacco of Enh2B or Enh7B or wild type tobacco (Havana SR1)

METHOD OF PROTECTING PLANTS BY INTRODUCING A GENE CODED FOR A PROTEIN WHICH ENHANCES VIRUS INFECTION OF HOST INSECTS

CROSS-REFERENCE TO RELATED APPLICATIONS

This is a continuation-in-part application of application Ser. No. 07/971,624 filed Nov. 4, 1992, now U.S. Pat. No. 5,475,090, which is a continuation-in-part of application Ser. No. 07/663,560 filed Mar. 4, 1991, now abandoned, which is a continuation-in-part application of application Ser. No. 07/313,226 filed Feb. 21, 1989, now abandoned.

FIELD OF THE INVENTION

This invention relates to the protection of plants from insects by introducing a gene that codes for a baculovirus protein which is characterized by enhancing the infectivity of baculoviruses. Such proteins termed herein as "enhancing" are found within the viral occlusion body, have a disruptive effect on the insect peritrophic membrane (PM) proteins, and/or interact with the midgut epithelium in such a manner as to permit the increased adsorption, penetration and uptake of virus particles by midgut cells with a resultant increase in insect host mortality.

BACKGROUND OF THE INVENTION

Present in the protein occlusion bodies (OBs) of some baculoviruses is a unique viral-encoded protein which enhances viral infection of the host insect. This protein is referred to herein as the virus enhancing factor (VEF) and/or as the synergistic factor (SF). Pest control Compositions comprising this factor and nuclear polyhedrosis viruses are the subject matter of U.S. Pat. Nos. 4,973,667 & 5,011,685.

Studies on the mode of action of the VEF isolated from *Trichoplusia ni* (cabbage looper) granulosis virus (TnGV) showed that the VEF caused rapid degradation of the peritrophic membrane which lines the midgut lumen of lepidopterous larvae. Larval bioassays suggested that this alteration made the peritrophic membrane more permeable to invading baculoviruses resulting in at least 25-fold increase in larval mortality (Derksen, A. G. S. and Granados, R. R. *Virology* 167: 242–250 (1988); and Peters, W. and Wiese, B. *J. Insect Physio.* 32: 43–49 (1986); both incorporated herein by reference).

The VEF gene was isolated and purified. It comprises a DNA molecule encoding a polypeptide of molecular weight 104 Kd and the protein is found in the granulin fraction of TnGV OBs purified by SEPHACRYL® S200 SUPERFINE (2.6×34 cm) column, possessing a biological activity and wherein said polypeptide has a total of 901 amino acid residues in the amino acid sequence of the polypeptide.

The gene encoding for viral enhancing factor (VEF) of TnGV was cloned from a lambda gtll expression library, and the complete nucleotide sequence determined. The VEF gene encodes a protein with a predicted molecular weight of 104 Kd which does not share homology to any previously reported proteins. The apparent promotor is located 4 bp upstream of the initiation codon and represents a consensus baculovirus late promoter (ATAAG). This has been confirmed by the identification of VEF mRNA in northern blots of infected larvae at 6 days but not 3 days post infection. Three repeats of the sequence 'TTACAAGA' which match the baculovirus late promoter in 4 of 5 nucleotide have been identified between 149 and 192 bp upstream of the initiation codon. While the function of these sequences is unknown, they are believed to be transcriptionally active since they diverge from the consensus promoter at the invariant 'T' position. Using the VEF gene as a probe in southern blots of genomic DNAs, homologous sequences have been identified in *Pseudaletia unipuncta* granulosis virus—Hawaiian strain (PuGV-H) and *Heliothis armigera* granulosis virus (HaGV) but not *Erinnyis ello* granulosis virus (EeGV), *Autographa californica* nuclear polyhedrosis virus (ACMNPV) or *Trichoplusia ni* nuclear polyhedrosis virus (TnSNPV). In addition, SDS-PAGE analysis of dissolved viral occlusion bodies have demonstrated proteins with a molecular weight similar to VEF in PuGV-H and HaGV.

The gene encoding the synergistic factor (SF) of PuGV-H was cloned and the complete nucleotide sequence determined. The SF gene encodes a protein with a predicted molecular weight of 104Kd which shares a 99.1% and 98.2% homology with the nucleotide and amino acid sequence of the viral enhancing factor (VEF) gene of TNGV, respectively. A majority of the differences in the amino acid sequences of the two viruses result from two reciprocal frameshifts which occur between nucleotide +1962 and +1985 of the SF gene. Both enhancin proteins have similar activity in neonate larvae of *Trichoplusia ni* (2.4 fold enhancement) and in vitro peritrophic membrane assays. Using a polyclonal antibody directed against TnGV VEF, 17 baculoviruses were screened by western blot hybridization. Cross reactive proteins are found in seven GVs isolated from 4 families of Lepidoptera. These putative enhancing proteins can be separated into 3 groups based on size: HaGV (lloKd); PuGV-H, *Pieris rapae* granulosis virus (PrGV), *Scotogramma trifolii* granulosis virus (StGV), and TnGV (104Kd); and *Cydia pomonella* granulosis virus (CPGV) and *Estigmene acrea* granulosis virus (80 Kd). The name "enhancin" has been proposed for these enhancing proteins.

Although the genes for some enhancins have been purified and isolated, a need still exists for transgenic plants that have been protected from insects by the introduction of an enhancin gene. Therefore, it is the primary object of the present invention to provide a transgenic plant and a method of protecting a plant by introducing an enhancin gene.

SUMMARY OF THE INVENTION

The above mentioned object of the present invention, which will hereinafter become more readily apparent from the following description, has been attained by first constructing a transfer plasmid that included an enhancin gene. The transfer plasmid was transferred to an *agrobacterium* through triparental mating of an *E. coli* strain with the enhancin transfer plasmid, the same *E. coli* strain with a mobilizing plasmid and the *agrobacterium*. The *agrobacterium* with the transfer plasmid was used to inoculate tobacco leafs. The inoculated tobacco leaves were sterilized and placed onto shooting medium. Once roots began to grow, the young shoots were transferred into pots. The tobacco plants were fed to insect larvae to screen the tobacco plants based upon the body weight gains of the insect larvae.

When daily changes of the body weight of *Pseudaletia separata* larvae fed with artificial diet mixed with the transgenic tobacco was compared with that of larvae fed with diet mixed with wild type tobacco, a delay of accumulation of body weight was found from 5 days after feeding until pupation. The maximum difference between the body weight of wild-type tobacco fed larvae and that of the transgenic tobacco strain Enh2B-fed larvae was 150 mg per larva at 15 days after feeding, the maximum difference between the body weight of wild type tobacco-fed larvae and that of transgenic tobacco strain Enh7B-fed larvae was 300 mg per larva at 15 days after feeding. At 13 days after feeding, a body volume of the larvae fed with diet mixed with Enh2B was much smaller than that of larvae fed with diet mixed with wild type tobacco. Some pupae in metaseteri or proseteri (half-larval and half-pupal morphology of pupa) were obtained in 33% of *P. separata* fed with diet mixed with Enh7B and in 53% of *P. separata* fed with diet mixed with Enh2B.

This data is similar to the results found when an enhancin protein was mixed with a larvae diet. Based upon this information it is clear that the tobacco plant has been protected by the insertion of the enhancin gene. While the current experiments were measured as a matter of larvae weight gain, not mortality, the larvae were not exposed to any pathogens. The larvae eating the protected tobacco would be far more susceptible to infection by pathogens due to the disruption of their peritrophic membrane by the enhancin.

A more complete understanding of the invention and its advantages will be apparent as the detailed description is considered in connection with the accompanying drawings.

BRIEF DESCRIPTION OF THE DRAWINGS

FIG. 1 shows the construction of the transfer vector plasmid pBI-Enh21 used in the triparental mating and the construction of the recombinant virus AcEnh 26.

FIG. 2 is a map of the TnGV EcoRI-K fragment and structure of the transfer vector pBI-Enh21.

FIG. 3 is a flow chart describing the triparental mating process.

FIG. 4 is a picture of pupae of *Pseudaletia separata* fed with transgenic tobacco of Enh2B or Enh7B or wild type tobacco (Havana SR1).

FIG. 5 is a picture of an example of a transgenic plant taught by the present invention.

DETAILED DESCRIPTION OF THE INVENTION

The following provides a detailed description of the specific methods and materials used to practice the method of protecting a plant by introducing an enhancin gene. It should be understood that modifications can be made to the procedures disclosed below that would still be anticipated by the present invention.

The first step to obtaining a transgenic plant was to construct a transfer plasmid that included an enhancin gene. The transfer plasmid was transferred to an *agrobacterium* through triparental mating of an *E. coli* strain with the enhancin transfer plasmid, the same *E. coli* strain with a mobilizing plasmid and the agrobacterium. The *agrobacterium* with the transfer plasmid was used to inoculate tobacco leafs. The inoculated tobacco leafs were sterilized and placed onto shooting medium. Once roots began to grow, the young shoots were transferred into pots. The tobacco plants were fed to insect larvae to screen the tobacco plants based upon the body weight gains of the insect larvae. Each of these steps is described in detail below.

Construction of the pBI-Enh21

The transfer plasmid, pBI-Enh21 was constructed from pVL-Enh21, which was co-selected with pVL-Enh26 during process of screening of hybrid DNA's from pVL1393/SmaI, XbaI and pBS-EnhH/HindIII, Bal31, XbaI. The pVL-Enh26 was used for homologous recombination with AcMNPVE2 DNA to obtain the recombinant AcMNPV expressing the enhancin. The construction scheme of pVL-Enh26 and pVL-Enh21 is shown in FIG. 1. The enhancin gene was excised from TnGV EcoRI-K fragment. The gene was then inserted in the Bluescript II plasmid (pBS). Then the plasmid DNA was digested with a endonuclease HindIII, digested by exonuclease Bal31, and a DNA fragment containing the open reading frame (ORF) of enhancin was excised by a endonuclease XbaI and inserted into the transfer vector pVL1393 to obtain pVL-Enh21 and pVL-Enh26.

As the first step of construction of pBI-Enh21, the plasmid DNA (pVL-Enh21) was digested with a endonuclease HindIII, digested by exonuclease Bal31, and a DNA fragment containing the open reading frame of enhancin was excised by a endonuclease XbaI. The protruding termini of the excised DNA fragment was filled with dNTPs and T4 DNA polymerase (DNA blunting kit, Takara Corp.). The pBI121 vector (Gus gene fusion system; purchased from Clone Tech. Corp.) was digested by a endonuclease SmaI and was ligated with the blunted DNA fragment indicated above. The selection of ligated DNA in correct orientation in respect to 35S promoter was done by restriction endonuclease digestion of minipreps of transformants (HB101—an *E. coli* strain). As shown in FIG. 2, pBI-Enh21 contains a DNA cartridge encompassing −21 to +2804 of TnGV enhancin gene at the cloning site SmaI of pBI121 immediately downstream of cauliflower mosaic virus 35S promoter and can be selected for by its Kanamycin resistance.

Triparental Mating

Triparental mating experiment was composed of several steps for transferring of pBI-Enh21 to *Agrobacterium tumefaciens* (LBA4404). Bacteria used for mating were HB101 carrying pBI-Enh21, HB101 carrying pRK2013, and LBA4404 carrying pAL4404. The HB101 carrying pRK2013 is the helper bacterium which assist in the transfer of pBI-Enh12 to LBA4404. A flow chart describing the mating process is shown in FIG. 3. Abbreviations are: $C^r$, Carbenicillin resistance; $K^r$, Kanamycin resistance; $S^r$, Streptomycin resistance; $C^+$, Carbenicillin (0.10 mg/ml); $K^+$, Kanamycin (0.15mg/ml); $S^+$, Streptomycin (0.05 mg/ml);

The HB101 carrying pBI-Enh12 was grown in LB medium containing Kanamycin (0.050 mg/ml). HB101 carrying pRK2013 was grown in the same medium described above. LBA4404 carrying pAL4404 was grown in AB medium containing Streptomycin (0.050 mg/ml). Table 1 shows the composition of the AB medium.

TABLE 1

Components of stock solutions required for preparation of AB medium[1] (/Stock solution 100 ml)

| | | |
|---|---|---|
| Solution 1 | $K_2HPO_4$ | 6 g |
| | $NaH_2PC_4$ | 2 g |
| Solution 2 | $NH_401$ | 2 g |
| | $MgSO_47H_2O$ | 0.3 g |
| | KCl | 0.3 g |
| | $CaCl_2$ | 0.3 g |
| | $FeSO_47H_2O$ | 5 g |
| Solution 3 | Glucose | 10 g |

[1]AB medium is composed of 5 ml of each stock solution 1, 2 and 3 and 85 ml of distilled water. To make AB plate 1.5% Bacto agar is added to AB medium.

The bacteria are streaked on the AB plate and incubated on the plate at 30° C. for 2 days. The bacteria grown are mixed on the plate by a glass rod and the incubation is continued for another 2 days at the same temperature. During this step, mating should be completed and the

*agrobacterium* carrying the enhancin gene was generated. Some bacteria from the plate were picked up and streaked onto the AB plate containing Streptomycin and Kanamycin of concentrations at 0.050 mg/ml. The plate was incubated at 30° C. for 2 days. A well-isolated colony (agrobacterium) was picked up from the plate and inoculated into AB broth containing the same antibiotics. The culture tube was incubated at 30° C. for 2 days by vigorous shaking.

Inoculation of Tobacco Leaves

*Nicotiana tabacum* cv. Havana SR1 (Streptomycin resistant strain) was employed for the host of *agrobacterium*. Young and well-extended leaves were cut and surface-sterilized in 70% ethanol for 10 min and 10% sodium hypochlorite solution (antimicrobial solution) for 15 minutes. Then they were dipped in distilled water three times and finally water drops were removed from them by sterilized paper towel. The leaves were cut into 2 cm squares. These pieces of tobacco were dipped in a culture of *agrobacterium* for 2–5 min., which had been prepared as described above. They were taken out individually, the extra agrobacterium was removed with the sterilized paper towel, and the piece of inoculated tobacco was placed on the MS1 agar plate. The plates were incubated at 26° C. for 2 days. Table 2 shows the components of stock solutions for preparations of MS medium. Table 3 shows how to prepare of the MS medium.

TABLE 2

Components of stock solutions for preparation of MS medium (/Stock solution 200 ml)

| Stock 1 | $NH_4NO_3$ | 33 G |
|---|---|---|
|  | $KNO_3$ | 38 g |
| Stock 2 | $MgSO_4 7H_2O$ | 7.4 g |
|  | $KH_2PO_4$ | 3.4 g |
| Stock 3 | $CaCl_2 2H_2O$ | 6.8 g |
| Stock 4 | $Na_2$-EDTA | 0.746 g |
|  | $FeSO_4 7H_2O$ | 0.556 g |
| Stock 5 | $H_3BO_3$ | 0.124 g |
|  | $MnSO_4 4H_2O$ | 0.446 g |
|  | $ZnSO_4 4H_2O$ | 0.172 g |
|  | KI | 0.017 g |
|  | $NA_2McO_4 2H_2O$ | 0.065 g |
| Stock 5 | $CuSO_4 5H_2O$ | 0.05 g |
|  | $CoCl_2 5H_2O$ | 0.05 g |
| Stock 6 | Thiamine-HCl | 0.008 g |
|  | Myo-Inositol | 7.2 g |
| Stock 7 | Naphthalene acetic acid (NAA) | 0.042 g |
| Stock 8 | 6-Benzyladenine (BAP) | 0.004 g |
| Stock 9 | 6-Benzyladenine (BAP) | 0.1 g |
| Stock 10 | Indole butyric acid (IBA) | 0.4 g |
| Stock 11 | Myo-Inositol | 2 g |
|  | Glycine | 0.04 g |
|  | Pyridoxine-HCl | 0.01 g |
|  | Nicotinic acid | 0.01 g |
|  | Thiamine-HCl | 0.02 g |

TABLE 3

Preparation of MS medium (/1 liter)

| 1) | Add 2 ml of Stocks to 200 ml of Stock 5. |
|---|---|
| 2) | In 300 ml flask, mix 10 ml of Stock 1, 2, 3, 4, 5, and 11 respectively. (For MS7, mix 8 ml of each Stock) |
| 3) | Add hormone stocks (hormones are shown in table 4) |
| 4) | Add 30 g of sucrose and fill up to 1 liter with distilled water. |
| 5) | Adjust to pH 5.8–0.2 with 1N KOH. |

TABLE 3-continued

Preparation of MS medium (/1 liter)

| 6) | Add 0.2% Gellan Gum and autoclave. |
|---|---|
| 7) | After cooling down to 50° C.–60° C., add filter-sterilized Kanamycin and Carbenicillin and coagulate in the culture pots. (Final concentration of antibiotics are: Kanamycin, 15 mg/ml; and Carbenicillin, 10 mg/ml.) |

Pieces of tobacco were transferred into MS1 medium containing carbenicillin at a concentration of 0.5 mg/ml (see tables 2, 3, and 4) to kill the *agrobacterium* at 26° C. for 2 days. The tobacco pieces were placed on MS4 agar plate (Carbenicillin, 10 mg/100 ml; Kanamycin, 15 mg/100) (see tables 2,3, and 4) with the cut surface down (agar side). They were incubated at 26° C. for 1 month to induce shooting from the callus. A list of the hormone concentrations is shown in table 4. Stocks 7, 8, 9 and 10 are hormone stocks for plant differentiation and are shown in table 2. MS1 is a callus medium. MS 4 is a shooting medium and MS 7 is a rooting medium.

TABLE 4

Hormone concentrations of MS medium

|  | Stock 7 | Stock 8 | Stock 9 | Stock 10 |
|---|---|---|---|---|
| MS1 | 10 ml | 10 ml | 0 ml | 0 ml |
| MS4 | 0.5 ml | 0 ml | 10 ml | 0 ml |
| MS7 | 0 ml | 0 ml | 0 ml | 10 µl |

The shoots were cut and placed on MS7 agar plate containing Carbenicillin and Kanamycin at concentrations of 0.10 mg/ml and 0.15 mg/ml, respectively (see tables 2,3, and 4). The MS7 agar is for rooting. When some roots were formed, the young tobacco plants were transferred into pots. Tobacco seedlings-are placed in an incubator at 28° C. at a photoperiod of 16 hours light and 8 hours dark.

Once seeds developed they were surface sterilized by suspending approximately 50 seeds in 3 ml of 70% EtOH for 10 min. Then the ethanol was removed with a pipette and 3 ml of 20% of antimicrobial solution was added. The seeds were treated for 5 min. The seeds were washed with distilled water 5 min. and placed onto the agar plate medium (MS8).

Effect of Transgenic Tobacco on the Growth of *Pseudaletia separata* Larvae.

Tobacco plants grown for 4 months after *agrobacterium* infection and wild type tobacco plants were freeze-dried and mixed with insect artificial diet at concentrations of 0.5% (w/w) or 1/0% (w/w). Preliminary experiment were designed to choose the amount of tobacco to be mixed in the diet, and it was found that 1.0% of wild type tobacco in the diet affected body weight gain of *P. separata* larvae, buL 0.5% did not in comparison with that of the larvae fed with diet only. Therefore, 0.5% of tobacco powder in the diet was employed through all the bioassay experiments.

Screening of Transgenic Tobacco Based on Body Weight Gains of Larvae.

We prepared leaf powder of 11 transformants of transgenic tobacco and assayed them as described above. Six transformants were effective and resulted in low levels of body weight gain of larvae. Table 5 shows the change in body weights of *Pseudaletia separata* larvae fed with artificial diet containing 0.5% tobacco powder from transgenic or wild type plants.

The most effective transformants were Enh2B and Enh7B. Growth of the larval stage was delayed one day by feeding diet mixed with Enh2B and in three days by feeding diet mixed with Enh7B, in comparison with that of the larvae fed with diet mixed with wild type tobacco.

TABLE 5

Change in body weights of *Pseudaletia separata* larvae fed with artificial diet containing 0.5% tobacco powder from transgenic or wild type plants

| To-bacco | Body weight (mg/larva) (days) | | | | | | | | |
|---|---|---|---|---|---|---|---|---|---|
| | 0 | 1 | 3 | 5 | 6 | 7 | 8 | 9 | 10 |
| exp. 1 | | | | | | | | | |
| wild type | 5 | 12 | 28 | 42 | 56 | 67 | 105 | 121 | 152 |
| Enh1A | 5 | 8 | 15 | 30 | 33 | 45 | 79 | 97 | 146 |
| Enh2A | 5 | 12 | 24 | 42 | 59 | 67 | 113 | 136 | 173 |
| Enh3B | 5 | 9 | 16 | 27 | 30 | 51 | 69 | 94 | 134 |
| Enh12C | 5 | 6 | 16 | 28 | 35 | 45 | 63 | 91 | 120 |
| Enh14A | 5 | 8 | 20 | 33 | 34 | 57 | 97 | 132 | 147 |
| exp. 2 | | | | | | | | | |
| wild type | 3 | 6 | 9 | 20 | 23 | 27 | 45 | 53 | 98 |
| Enh2B | 3 | 6 | 3 | 16 | 22 | 26 | 36 | 38 | 50 |
| Enh4 | 3 | 9 | 12 | 24 | 26 | 38 | 70 | 73 | 85 |
| Enh7B | 3 | 5 | 5 | 9 | 12 | 16 | 19 | 22 | 33 |
| Enh3A | 3 | 6 | 10 | 15 | 21 | 24 | 35 | 41 | 68 |
| Enh10 | 3 | 7 | 8 | 15 | 16 | 24 | 40 | 42 | 59 |
| Enh12B | 3 | 3 | 5 | 11 | 11 | 20 | 38 | 38 | 65 |

| To-bacco | Body weight (mg/larva) (days) | | | | | | | | |
|---|---|---|---|---|---|---|---|---|---|
| | 11 | 12 | 13 | 14 | 15 | 16 | 17 | 18 | 19 |
| exp. 1 | | | | | | | | | |
| wild type | 194 | 240 | 378 | 471 | 646 | 655 | P | | |
| Enh1A | 175 | 213 | 340 | 451 | 619 | 722 | P | | |
| Enh2A | 202 | 250 | 316 | 440 | 584 | 639 | P | | |
| Enh3B | 175 | 256 | 312 | 505 | 593 | 620 | P | | |
| Enh12C | 177 | 262 | 375 | 485 | 569 | 632 | P | | |
| Enh14A | 275 | 253 | 425 | 556 | 574 | P | | | |
| exp. 2 | | | | | | | | | |
| wild type | 121 | 161 | 237 | 336 | 453 | 552 | 580 | P | |
| Enh2B | 71 | 93 | 138 | 221 | 294 | 367 | 481 | 554 | Γ |
| Enh4 | 101 | 117 | 195 | 171 | 317 | 498 | 588 | 608 | P |
| Enh7B' | 42 | 52 | 71 | 138 | 167 | 228 | 333 | 421 | 460 |
| Enh3A | 111 | 145 | 139 | 213 | 331 | 388 | 525 | 577 | P |
| Enh10 | 94 | 121 | 155 | 230 | 408 | 485 | 662 | 717 | P |
| Enh12B | 144 | 154 | 219 | 335 | 529 | 870 | P | | |

[1]The body weight of larvae eating Enh7B with their diet was 610 mg at 20 days and they pupated at 21 days.

Effect of Transgenic Tobacco Enh2B and Enh7B on the Growth of *P. separata* Larvae.

Figure 4:
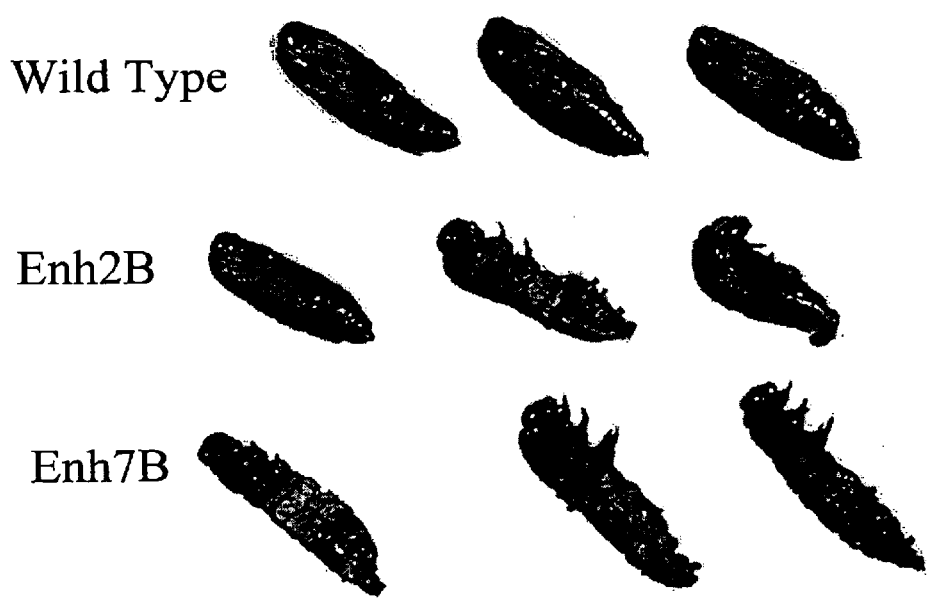

When daily changes of a body weight of *P. separata* larvae fed with diet mixed with Enh2B or diet mixed with Enh7B was compared with that of the larvae fed with diet mixed with wild type tobacco, a delay of accumulation of body weight was found from 5 days after feeding. The maximum difference between the body weight of wild-type tobacco fed larvae and that of Enh2B fed larvae was 150 mg per larva at 15 days after feeding, and the maximum difference between the body weight of wild type tobacco fed larvae and that of Enh7B fed larvae was 300 mg per larva at 15 days after feeding. At 13 days after feeding, the body volume of the larvae fed with diet mixed with Enh2B was much smaller than that of larvae fed with diet nixed with wild type tobacco. Some pupae in metaseteri or proseteri (half-larval and half-pupal morphology of pupa) were obtained in 33% of *P. separata* fed with diet mixed with Enh7B and in 53% of *P. separata* fed with diet mixed with Enh2B. FIG. 4 is a picture of pupae of *P. separata* fed with transgenic tobacco of Enh2B or Enh7B or wild type tobacco (Havana SR1) which shows this effect.

Some Properties of Transgenic Tobacco

Figure 5:

FIG. 5 is a picture of an example of a transgenic plant taught by the present invention. Basically, up to now, significant differences between the wild type tobacco and the transgenic tobacco of enhancin were not found in respect with growing speed, number of leaves, number of flowers, height of plant, shape of leaves, and color or plant etc. In the steps of surface sterilization of seeds before placing them on agar medium, about twice as many floating seeds were observed when washing transgenic tobacco than in wild type tobacco, indicating that rate of shooting seeds in transgenic tobacco may be less than that of wild type tobacco. But, this difference may not be due to the presence of the enhancin gene in tobacco, since wild type tobacco seeds were obtained elsewhere and transgenic tobacco seeds were obtained in our lab.

Effect of Purified Enhancin on the Growth of *Trichoplusia ni* Larvae

Purified enhancin from *T. ni* granulosis virus was mixed with artificial diet and fed to *T. ni* neonate larvae (freshly hatched). This is the same enhancin expressed in the transgenic plants described above.

The VEF was purified from TnGV by first dissolving TnGV capsules ($1.7 \times 10^2$/ml) in 0.05 M $Na_2CO_3$, pH 10.5, for 15 min. at room temperature. The capsule mixture was layered on a 20% sucrose cushion and centrifuged 150,000 g for 45 min. at 4° C. The supernatant was removed and applied to a Sephacryl S-200 column (Pharmacia LKB Biotechnology Inc., Piscataway, N.J.) (1.5 cm×100 cm) equilibrated with 0.05 M $Na_2CO_3$. The column was eluted with 0.05 M $Na_2CO_3$ at a flow rate of 0.5 ml/min.

Aliquots of 2 ml were collected and tested for the presence of VEF by SDS-PAGE (Laemmli, 1970). Fractions containing VEF were pooled and concentrated using a Centriprep (Amicon, Beverly, Mass.) concentrator, and the final protein concentration was determined by the Bradford assay (Bradford, 1976). Aliquots of the VEF were frozen at −20° C. for storage.

A high wheat germ diet was used for the experiments. For each experiment, twenty 1 oz. diet cups (3 ml per cup) were used as controls. The diet containing VEF was made by measuring 60 ml of the hot diet into a small blender and stirring gently with a glass rod to cool the diet and avoid the solidifying of the surface of the diet. Cool wet paper towels can be used to cover the outside wall of the blender to help the diet cool to 40–45° C. (measured by a sterile thermometer). The volume of VEF and the diet should total about 65 ml to make 20 cups, which means that about 5 ml of VEF should be added. More importantly, the proper dose of VEF should be added depending upon the particular concentration of the VEF preparation. For example a 0.2 mg/ml diet dose of VEF would be prepared by adding 13 mg of VEF to 65 ml of total diet (after VEF added).

The diet preparation should be sufficient to make twenty 1 oz cups (3 ml per cup) by manual pipetting the diet into the cups. About 6 ml of the diet should be aspirated using a modified 10 ml sterile pipette (larger bore) each time as quickly as possible. When the diet cools and solidifies, 40 *T. ni* neonate larvae were transferred into separate cups with a sterile fine paint brush (20 larvae (cups) for controls and 20 larvae (cups) for VEF treatment). The cups were covered with their lids, sealed with parafilm and placed in a 28° C. incubator.

The data from these experiments show that the average weight of larvae fed on the enhancin/diet was less than the control fed on artificial diet only (see table 6—differences in average weight are shown in parenthesis). Table 6 shows the average weight of the larvae at 3, 6 and 8 days post feeding (pf).

TABLE 6

Change of body weights of *Trichoplusia ni* larvae fed with artificial diet containing VEF (enhancin)

| Exp. No. | Treatment | # of Larvae | Avg. wt. (mg) of larvae (days pf) | | |
|---|---|---|---|---|---|
| | | | 3 | 6 | 8 |
| 1 | 0.15 mg/ml | 7 | 3.9 ± 0.6 | 80.4 ± 19.5 | 205.6 ± 100.4 |
| | control | 7 | 5.4 ± 1.9 | 105.6 ± 54.4 | 236.1 ---- |
| | | | (1.5) | (25.2) | (30.5) |
| 2 | 0.20 mg/ml | 20 | 4.7 ± 0.9 | 80.3 ± 17.1 | 222.3 ± 68.5 |
| | control | 20 | 5.8 ± 1.7 | 122.1 ± 39.3 | 231.2 ± 95.9 |
| | | | (1.1) | (41.8) | (8.9) |
| 3 | 0.20 mg/ml | 20 | 3.3 ± 0.5 | 83.1 ± 37.8 | 182.9 ± 95.6 |
| | control | 20 | 4.82 ± 1.3 | 130.5 ± 47.4 | 215.0 ± 99.3 |
| | | | (1.5) | (47.4) | (32.1) |
| 4 | 0.20 mg/ml | 20 | 3.4 ± 0.4 | 95.4 ± 8.7 | 242.5 ± 51.8 |
| | control | 20 | 4.0 ± 0.3 | 105.1 ± 6.0 | 273.1 ± 31.1 |
| | | | (0.6) | (9.7) | (30.6) |

Table 7 shows the number of prepupae and pupae at 8 and 10 days post feeding respectively. the difference in weight between both treatments is retardation in growth as seen by the time of appearance of prepupae or pupae in treated and control insects. In all cases, the appearance of prepupae and pupae in the enhancin-treated insects was retarded. The data suggests that enhancin (VEF) at concentrations of 0.15 to 0.20 mg/ml of diet can alter the development of *T. ni* larvae and support the data from the transgenic plant research.

TABLE 7

Number of prepupae and pupae of *Trichoplusia ni* larvae fed with artificial diet containing VEF (enhancin)

| Exp. No. | Treatment | # of Larvae | # of prepupae & pupae (days pf) | |
|---|---|---|---|---|
| | | | 8 (prepupae) | 10 (pupae) |
| 1 | 0.15 mg/ml | 7 | 3 | 5 |
| | control | 7 | 6 | 7 |

TABLE 7-continued

Number of prepupae and pupae of *Trichoplusia ni* larvae fed with artificial diet containing VEF (enhancin)

| Exp. No. | Treatment | # of Larvae | # of prepupae & pupae (days pf) | |
|---|---|---|---|---|
| | | | 8 (prepupae) | 10 (pupae) |
| 2 | 0.20 mg/ml | 20 | 4 | 20 |
| | control | 20 | 12 | 20 |
| 3 | 0.20 mg/ml | 20 | 2 | 15 |
| | control | 20 | 10 | 18 |
| 4 | 0.20 mg/ml | 20 | 0 | 17 |
| | control | 20 | 11 | 20 |

The teachings of the present invention show that an enhancin gene can be engineered to be expressed in transgenic plants and as insects feed on these plants, they ingest a constant dose of the enhancin. While the exact effect of this on the infectivity of pathogens is undetermined, it can be hypothesized that prolonged disruption of the peritrophic membrane (PM) may allow opportunistic microbes to infect and kill the insects. Therefore the use of viral insecticides or other natural biocides could prove to be a commercially viable alternative to chemical pesticides for transgenic plant crops.

It was recently found that the viral factor increases the efficiency of Bt delta endotoxin by removing a major mechanical barrier—the PM. The larvae fed the enhancin (either isolated enhancin or the transgenic tobacco) did not pupate normally. The larvae showed irregular morphology of half larva and half pupae, suggesting a hormonal disturbance caused by the transgenic tobacco.

Based upon the teachings herein, enhancin genes can be introduced into a variety of plants. The introduction of an enhancin gene into plants is an effective method of protecting them from insects due to the disruption of their normal life cycle.

The foregoing description has been directed to particular embodiments of the invention in accordance with the requirements of the Patent Statutes for the purposes of illustration and explanation. It will become apparent, however, to those skilled in the art that many modifications and changes will be possible without departure from the scope and spirit of the invention. It is intended that the following claims be interpreted to embrace all such modifications.

We claim:

1. One or more plant cells comprising a polynucleotide that encodes a baculovirus protein designated as an enhancin, wherein said enhancin is expressed in said plant cells.

2. The plant cell of claim 1 wherein said enhancin is characterized by having a disruptive effect on the insect peritrophic membrane proteins or interacting with the midgut epithelium in such a manner as to permit the increased adsorption, penetration, and uptake of virus particles by midgut cells with a resultant increase in host mortality.

3. The plant cell of claim 2 wherein said plant is a tobacco plant.

4. The plant cell of claim 3 wherein said plant is of the species *Nicotiana tabacum*.

5. A method of delivering a substance that disrupts peritrophic membranes to insects comprising the step of introducing a polynucleotide that encodes a baculovirus protein designated as an enhancin into a plant that is eaten by said insect, wherein said enhancin is expressed in a portion of said plant.

6. The method of claim 5 wherein said enhancin is characterized by having a disruptive effect on the insect peritrophic membrane proteins or interacting with the midgut epithelium in such a manner as to permit the increased adsorption, penetration and uptake of virus particles by midgut cells with a resultant increase in host mortality.

7. The method of claim 6 wherein said plant is a tobacco plant.

8. The method of claim 7 wherein said plant is of the species *Nicotiana tabacum*.

* * * * *

SEQUENCE LISTING

<160> NUMBER OF SEQ ID NOS: 2

<210> SEQ ID NO 1
<211> LENGTH: 3555
<212> TYPE: DNA
<213> ORGANISM: Trichoplusia ni Granulosis Virus

<400> SEQUENCE: 1

```
cagcgcgaaa acggttggtg ccaattactg gtatattgct atgatcgagt cacgtcataa      60
gggtcgattc gcgacggtct cccacgtggc cttccattga ggtttacgtg tttgtgtatg     120
cgtgcgagtg tttttataac ccaaaaactc agccacaccg tgtccaccgt acatatactt     180
```

-continued

```
gtccttttcc aattccacaa tccaaatttc cgcagaaact cctccaatgt tgcacgattt    240
ttttacaaga gtcattttgc acgtttacaa gaaatttatt acaagattag ctgcttgtga    300
taaaggtctg cacgagatga gattcaaata cgtaatgaga attgcgtgat ttgcacgagt    360
ttatatagca taatttgcta ggaatgtctg ttggtttgtg atgtttaggt gttcgctgca    420
ttaattataa gactatgtcg tacaaagtga ttgtacccgc taccgtgcta ccgccgtggc    480
tcagagtcgg tgagaattgg atattcgcaa gacacagacg caccgaggtg ggagtcgttc    540
taccggcgaa cacgaaattt cgtgtacgag cagatttctc tagggccggc ttcacccgac    600
ccgtaatagt gcgcctcttg aacaacaacc gtagcactga acgagaaatc aacttgaaca    660
acgaccaatg gatggaggtg gagcatgcgc acgagagtgt gcctttcgta gattggctgg    720
tgggcgaaaa gaacactatg gccgaagtgt attttgaaat cgacggacca cacataccgc    780
tacccgtgta cgtgttcaac acgagacccg tcgaacactt taagagcgag tatcgccaaa    840
gttcgtctgg ctactgcttt ctatatttgg acctggtctg tatgttggta ccgcccgcta    900
gcaaaaacgc tttattggac gtgaacattt tcgagcttca tcaattttat aacgaaatca    960
ttaattacta tgatgacctg tgcggcttgg tcgaggatcc atacgcagac actgtcgatt   1020
cgaatttacc caacaaggct gctttcgtga agctgatgc tggcggtccg ggtggtgcgt   1080
attatggacc attttggacg gcaccggcga gctcaaacct tggtgattac ctcagaatat   1140
cgccgaccaa ctggatggta attcacgagc tgggtcatgc atacgatttt gtgtttaccg   1200
tcaacactat actcattgaa atttggaaca actcttttgc gatcgcatcc aatacaagtg   1260
gatgaacaaa attaaaagac aacaactggc tcgcgtctat gaaaatagac gaccgcagaa   1320
agaggcgacc attcaggcgc tgatcgacaa taacagcccg ttcgataatt ggggcttttt   1380
tgagaggctg ataatattca cgtggctgta caacccgcaa agaggactag acacattgcg   1440
taacatcaac cattcgtaca gggtgcacgc cacccgcaac tcttctatac cgtacccgca   1500
aatatggtca tggctaacga cttctgctta cgacaacttt tggttatatt ttaatttggt   1560
aggcgtgtac ccggcagact tttacgtaaa cgaacacaac aaagttgttc atttcaatct   1620
acacttgaga gctttggcgt tggggcagag tgtgcgttat cccattaaat atataattac   1680
agactttgat ctggtgagca aaaactacga cattaaacag tatttagaga gtaatttcga   1740 tctggtttata ccagaagaat tgcggcagac cgatttgttg gcggacgtga gggtggtttg   1800
tgtgattgac gatccgtcgc agattgtggg cgaaccgttt agcgtgtacg acgggaacga   1860
gcgagtgttc gagagtacgg tggccacgga cggaaacatg tatctggtgg cgtgggtcc    1920 gggagtgtac acgttgcgtg cgccacgcgg caaaaacaaa cgctacaaac tccatttggc   1980
acattcgccc agagagcccg ttcatccggc caacgaccac atgtatctgc tcgtgacgta   2040
tccctactac aatcaaacgt tgacatacac accgtacgta aattctgacc tagccgtcga   2100
catggctcat tgttcggca gcaacgatcg taggtatgta gccacgatat atttcaatcc    2160
attcgaacaa acagtcaccg tacatctaaa caatattcgt gccggtcgtg aaaacaacac   2220
taccctgtac tttgaaatgg taattagcaa cccgttcaac gggcagagcc aaactttcac   2280
tatactcgaa gacaatccca ctttacgaca aggctactac aaatttgacg tggtcacgta   2340
cagctccata aggctgaata tgagcgtcgc gggtcggcta ttatttcggc gatacatttt   2400
tgccggaggt accaccacgc tgaccatgtt cccaaatcaa gtacttgagc ccaatttgtt   2460
tccagacggt tccgccttga ataggacatt ggcacgacta agagaacagg ccgccttcct   2520
```

-continued

```
agataattat tcacaactta tgtatattga aaacgagttg cgcgacacga tttatttggc      2580
ctcccagttg gtagatcctg cgtcagacga atttgtaaag tattatccag actacttcag      2640
agatccgcac acgtacgtgt acttgtttcg tttcagaggt ctgggtgatt cgtgttatt       2700 agacttgcag attgtaccat tgctaaattt ggccactgta cgtatagcca acatccaaaa      2760
cggtccccac tcgtacttcg atactttgta ttttaaagtg gagttgcgcg acacaaacgg      2820
tgcgattgtg ttttcgtatt cgcgccgtgg caacgagccg atgacacccg aacaccataa      2880
atttgaagtg tacagtggtt acaccgtaga attgttcatg cgggaacccg gtaatcgatt      2940
acaattgatt gtgaacaaaa tgcttgacac agcgttgccg tctactcaaa acattttcgc      3000
tcgcatcacc gacactcaat tagtggtggg ggatacgagc attgaagata accttgtaac      3060
gagtattaat gtagattgtg cgacgacga caaccaaaag ataagagttg tggaaacgtt       3120
aaaaatgata gcgttctaat aacgttcaac agtcagttat cgactgtcgc cgcgacgaca      3180
tgacactggt gggtgtagta gttttgcgtgc tgttgttatc gtctgtagac ggttattcgt     3240
tttattcgtc gattgaagcc ctgcttttga acgatcgcac acaactttgc ataggcgact      3300
gttacgaacg caatggccag catttgtgtg ccagcacgtg gtcgggatca gagtctcggt      3360
gcataagtgt tttcaacaag accaaacact atcgtacgga gactaacgga aaatgcataa      3420
gtaactgtgc caacttcaac aactacgccc acgaatggtg tgccgtgtcc cggtcgaaat      3480
ggggccgttg cagcagacga ctggcgctca cagcgacacg aacacacgcc acccacaaca      3540
agttcaagac atgtg                                                       3555
```

<210> SEQ ID NO 2
<211> LENGTH: 3572
<212> TYPE: DNA
<213> ORGANISM: Pseudaletia unipuncta Granulosis Virus

<400> SEQUENCE: 2

```
atgcatacac accagcttct gttataaata ctgtattaaa ttgccaatta gatggaagtt      60
gtgtatttat aaacgttcgg tcctgtatat cttgccaatg atttgcgcca tatttgtttt      120
acatgatctc ggatagcttt tgaggatta gtgtatccca aaaattgcgc ataccatgt        180 ccgcgtacat aaatttatca ttttccactt ccacaatcca aatttccgca gaaactcctc      240
caatgttgca cgatttttt acaagagtca ttttgcacgt ttacaagaaa tttattacaa       300
gattagctgc ttgtgataaa ggtctgcacg agatgagatt caaatacgta atgagaattg      360
cgtgatttgc acgagtttat atagcataat ttgctaggaa tgtctgttgg tttgtgatgt      420
ttaggtgttc gctgcattaa ttataagact atgtcgtaca aagtgattgt acccgctacc      480
gtgctaccgc cgtggctcag agtcggtgag aattggatat tcgcaagaca cagacgcacc      540
gaggtgggag tcgttctacc ggcgaacacg aaatttcgtg tacgagcaga tttctctagg      600
gcgggcttca cccgacccgt aatagtgcgc tccttgaaca caaccgtaa tactgaacga       660 gaaatcaact tgaacaacga ccaatggatg gaggtggagc atgcgcacga gagtgtgccg      720
tttgtcgatt ggccggtggg cgaaaggaac attatggccg aagtgtattt tgaaatcgac      780
ggaccacaca taccgctgcc cgtgtacgtg ttcaacacga gacctgtcga cactttaag       840 agcgagtatc gccaaagttc gtctggctac tgctttctat atttggacct ggtctgtatg      900
ttggtaccgc ccgctagcaa aaacgcttta ttggacgtga acattttcga gcttcatcaa      960
ttttataacg aaatcattaa ttactatgat gacctgtgcg gcttggtcga ggatccatac      1020
gcagacactg tcgattcgaa tttacccaac aaggctgctt tcgtgaaagc tgatgctggc      1080
```

-continued

```
ggtccgggtg gtgcgtatta tggaccattt tggacggcac cggcgagctc aaaccttggt    1140
gattacctca gaatatcgcc gaccaactgg atggtaattc acgagctggg tcatgcatac    1200
gattttgtgt ttaccgtcaa cactatactc attgaaattt ggaacaactc tttatgcgat    1260
cgcatccaat acaagtggat gaacaaaacc aaaagacaac aactggctcg cgtctatgaa    1320
aatagacgac cgcagaaaga ggcgaccatt caggcgctga tcgacaataa cagcccgttc    1380
gataattggg gctttttttga gaggctgata atattcacgt ggctgtacaa cccgcaaaga    1440
ggactagaca cattgcgtaa catcaaccat tcgtacaggg tgcacgccac ccgcaactct    1500
tctataccgt acccgcaaat atggtcatgg ctaacgactt ctgcttacga caacttttgg    1560
ttatatttta atttggtagg cgtgtacccg gcagactttt acgtaaacga acacaacaaa    1620
gttgttcatt tcaatctaca cttgagagct ctggcgttgg ggcagagtgt gcgttatccc    1680
attaaatata taattacaga ctttgatctg gtgagcaaaa actacgacat taaacagtat    1740
ttagagagta atttcgatct ggttatacca gaagaattgc ggcagaccga tttgttggcg    1800
gacgtgaggg tggtttgtgt gattgacgat ccgtcgcaga ttgtgggcga accgtttagc    1860
gtgtacgacg ggaacgagcg agtgttcgag agtacggtgg ccacggacgg aaacatgtat    1920
ctggtgggcg tgggtccggg agtgtacacg ttgcgtgcgc cacgcggcaa aaacaaacgc    1980
tacaaactcc atttggcaca ttcgcccaga gagcccgttc atccgccaaa cgaccacatg    2040
tatctgctcg tgacgtatcc ctactacaat caaacgttga catacacacc gtacgtaaat    2100
tctgacctag ccgtcgacat ggctcatttg ttcggcagca acgatcgtag gtatgtagcc    2160
acgatatatt tcaatccatt cgaacaaaca gtcaccgtac atctaaacaa tattcgtgcc    2220
ggtcgtgaaa acaacactac cctgtacttt gaaatggtaa ttagcaaccc gttcaacggg    2280
cagagccaaa ctttcactat actcgaagac aatcccactt tacgacaagg ctactacaaa    2340
tttgacgtgg tcacgtacag ctccataagg ctgaatatga gcgtcgcggg tcggctatta    2400
tttggcgata catttttgcc ggagggtacc accacgctga ccatgttccc aaatcaagta    2460
cttgagccca atttgtttcc agacggttcc gccttgaata ggacattggc acgactaaga    2520
gaacaggccg ccttcctaga taattattca cagcttatgt atattgaaaa cgagttgcgc    2580
gacagcattt atttggcctc ccagttggta gatcctgcgt cagacgaatt tgtaaagtat    2640
tatccagact acttcagaga tccgcacacg tacgtgtact tgtttcgttt cagaggtctg    2700
ggtgattttg tgttattaga cttgcagatt gtaccattgc taaatttggc aactgtacgt    2760
atagctaaca accacaacgg tccccactcg tacttcgata cttttgtattt taaagtggag    2820 ttgcgcgaca caaacggtgc gattgtgttt tcgtattcgc gccgtggcaa cgagccgatg    2880
acacccgaac accataaatt tgaagtgtac agtggttaca ccgtagaatt gttcatgcgg    2940
gaacccggta atcgattaca attgattgtg aacaaaatgc ttgacacagc gttgccgtct    3000
actcaaaaca ttttcgctcg catcaccgac actcaattag tggtggggga tacgagcatt    3060
gaagataacc ttgtaacgag tattaatgta gattgtggcg acgacgacaa ccaaaagata    3120
agagttgtgg aaacgttaaa aatgatagcg ttctaataac gttcaacagt cagttatcga    3180
ctgtcgccgc gacgacatga cactggtggg tgtagtagtt tgcgtgctgt tgttatcgtc    3240
tgtacacggt tattcgtttt attcgtcgat tgaagccctg cttttgaacg atcgcacaca    3300
actttgcata ggcgactgtt acgaacgcaa tggccagcat ttgtgtgcca gcacgtggtc    3360
gggatcagag tctcggtgca taagtgtttt caacaagacc aaacactatc gtacggagac    3420
```

| | |
|---|---|
| taacggaaaa tgcataagta actgtgccaa cttcaacaac tacgcccacg aatggtgtgc | 3480 |
| cgtgtcccgg tcgaaatggg gccgttgcag cagacgactg gcgctcacag cgacacgaac | 3540 |
| acacgccacc cacaacaagt tcaagacatg tg | 3572 |